United States Patent
Wolter

(10) Patent No.: US 8,460,347 B2
(45) Date of Patent: Jun. 11, 2013

(54) LOAD CARRIER FOR A BONE FIXATION SYSTEM

(76) Inventor: Dietmar Wolter, Hoisdorf (DE)

( * ) Notice: Subject to any disclaimer, the term of this patent is extended or adjusted under 35 U.S.C. 154(b) by 697 days.

(21) Appl. No.: 12/520,796

(22) PCT Filed: Dec. 11, 2007

(86) PCT No.: PCT/EP2007/010821
§ 371 (c)(1),
(2), (4) Date: Nov. 25, 2009

(87) PCT Pub. No.: WO2008/077482
PCT Pub. Date: Jul. 3, 2008

(65) Prior Publication Data
US 2010/0082069 A1    Apr. 1, 2010

(30) Foreign Application Priority Data

Dec. 20, 2006 (DE) .......... 10 2006 060 935

(51) Int. Cl.
*A61B 17/80* (2006.01)
(52) U.S. Cl.
USPC ........... 606/298; 606/280; 606/281; 606/283; 606/286; 606/76

(58) Field of Classification Search
USPC .................... 606/283, 284, 76, 286
See application file for complete search history.

(56) References Cited

U.S. PATENT DOCUMENTS

| 3,463,148 A | 8/1969 | Treace |
| 4,219,015 A | 8/1980 | Steinemann |
| 4,683,878 A * | 8/1987 | Carter ............................. 606/97 |
| 5,709,686 A * | 1/1998 | Talos et al. .................... 606/281 |

FOREIGN PATENT DOCUMENTS

| DE | 2806414 | 10/1978 |
| EP | 0266146 | 5/1988 |
| WO | WO-01/19264 | 3/2001 |

OTHER PUBLICATIONS

International Search Report directed to counterpart application No. PCT/EP2007/010821 mailed Mar. 27, 2008; 4 pages.

* cited by examiner

*Primary Examiner* — Andrew Yang
(74) *Attorney, Agent, or Firm* — Morrison & Foerster LLP

(57) ABSTRACT

The subject matter of the invention is a load carrier for a bone fixation system, with a locally varying material strength with unchanging material elasticity, and a method for producing such a load carrier. The load carrier, matched in view of the load flow acting on the fixation system, can also be used in critical anatomical regions, e.g. for hand implants.

23 Claims, 1 Drawing Sheet

LOAD CARRIER FOR A BONE FIXATION SYSTEM

REFERENCE TO RELATED APPLICATIONS

This application is a national stage application under 35 USC 371 of International Application No. PCT/EP2007/010821, filed Dec. 11, 2007, which claims the priority of German Patent Application No. 10 2006 060 935.2, filed Dec. 20, 2006, the contents of which prior applications are incorporated herein by reference.

FIELD OF THE INVENTION

The invention relates to a load carrier for a bone fixation system, and a method for its production.

BACKGROUND OF THE INVENTION

Fixation systems for bones with a load carrier and bone screws which can be inserted and fixed in the load carrier, e.g. plate, nail and fixator systems, are used in order to surgically connect bone fragments with one another.

Bone screw and bone plate can in this case also be interlocked with one another at a fixed angle. This new generation of implants, having a multi-directionally fixed-angle connection between the screw head and the bone plate hole, are distinguished by a higher capability with unchanging or reduced material expenditure.

Investigations have shown that the load flow in these fixed-angle systems is characterized in that the loads are not transferred uniformly, via the screws, from a bone fragment to the bone plate and, via the plate and the screws, to the other bone fragment, but that the first screw adjacent to the fracture and the plate components surrounding the plate hole transfer approximately 50-60% of the overall forces and loads, the following, that is to say second, screw and the plate components surrounding the plate hole transfer 20-30%, and the next, that is to say third, screw and the plate components surrounding the plate hole transfer approximately 10%.

The reason why this fact is of great importance is because, when assuming the previously used plate design, there is a threat of failure of the system in the region of the first plate hole adjacent to the fracture, to be precise in such a fashion that either the neck region of the screw or the plate, level with this first hole, deforms or breaks as a result of overloading or fatigue.

This problem is solved in European Patent 1 211 994 B1 by virtue of the fact that the load carrier is strengthened by widening or has a region with stronger material. Said material is strongest in the region of the first hole for the bone screw, located proximally to the fracture or instability zone; it is less strong in the region of the second, distally subsequent hole; and weakest in the region of the third, distally subsequent hole.

Furthermore, it is possible to react by simultaneously increasing the thickness of the screw core, and hence the screw, so that the load stability of the respective plate hole/screw unit constitutes an addition of the strength of the plate and the strength of the screw.

The disadvantage lies in larger dimensions and thus an increased cover of the bone surface, and increased lifting of the soft parts which come to rest above the plate. This is the equivalent of increasing the surgical wound and hence also of increasing the complexity of the surgical procedure. In certain areas of application, in which the size of the implants is limited by the anatomy, e.g. in the region of the hand, the fixation systems disclosed in EP 1 211 994 B1 can hardly be used, not least because of the additional widening or increased thickness of the load carrier.

SUMMARY OF THE INVENTION

The invention is based on the object of providing a load carrier for a bone fixation system which avoids the above-mentioned disadvantages as far as possible.

The invention has realized that an integral load carrier, with locally varying material strengths in different regions of the load carrier and with unchanging material elasticity, can be adapted in view of the load flow on the implant. If the material strength of the load carrier is matched to the respective load of the regions applied to the different regions of the load carrier, the widening and increase in thickness of the load carrier cross section disclosed in EP 1 211 994 B1 can be dispensed with to the greatest possible extent and the load carriers, which thus have smaller dimensions but are nevertheless reinforced, can be used in critical regions as well, e.g. for hand implants.

The invention has furthermore realized that load carriers composed of a metal or a metal alloy, preferably titanium or a titanium alloy, are particularly suitable as the load carrier. The material properties of this material can be changed particularly well by material compression such that this results in an increase in the strength of the load carrier, corresponding to the force and load flow, while the elasticity remains unchanged. The unchanging material elasticity, that is to say the capability to oppose a load which acts on it with mechanical resistance and to return to its original shape after unloading, is an essential feature of the load carrier. As a result of the unchanging elasticity, even in regions of increased material strength, the load carrier according to the invention does not have regions with more brittle material which would be the first to react with failure (breakage) when loaded.

The load carrier according to the invention, which is distinguished, on the one hand, by locally varying material strengths and, on the other hand, by unchanging material elasticity, can be produced in a shaping press-form tool by deforming a load carrier semi-finished product which has an increased volume of material in the regions where the load carrier is intended to have increased material strength compared to the regions which are intended to have lower material strength. The press-form tool has an upper tool and a lower tool between which the load carrier semi-finished product is deformed. The surfaces of the upper tool and the lower tool, which come into contact with the load carrier during the deformation, can have planar surfaces or inward or outward molding, which, after the deformation in the press-form tool, can be found mirror-symmetrically on the surface of the load carrier, preferably in the regions which are intended to have high material strength.

Expediently, the deformation is a cold forming, that is to say, in the case of metal materials, a shaping deformation at a temperature significantly below the recrystallization temperature, for example at room temperature. In the process, the deformation load acting on the semi-finished product in the press-form tool reduces the height and/or width and cross section of the semi-finished product, respectively, in the regions which are intended to have high material strength. In the process, a uniaxial pressure can be applied to the load carrier semi-finished product, as is the case in upsetting, or a biaxial pressure can be applied, as is the case in rolling. When using a titanium-containing material, the latter is advantageous because, in addition to the material being compressed, the fibers align in the rolling direction during the rolling, which allows an additional increase in stability because the fibers can be aligned in a targeted fashion in the direction of the main loading axis of the load carrier by means of a predetermined rolling direction.

Expediently, the load carrier according to the invention has at least two adjacent holes for holding bone screws. The holes are preferably provided with a means suitable for interlocking with a bone screw, preferably a material lip. This can already be taken into account during the deformation of the load carrier semi-finished product in the method according to the invention for producing such a load carrier, by the upper tool and/or lower tool having receptacles, preferably bores, which prevent significant material hardening in the regions of the load carrier semi-finished product which lie opposite the receptacles during the deformation in step b) and in which holes, which are intended to be inserted, for attaching the load carrier to the bone are provided.

The corresponding holes can be bored through the regions which are provided for the bone screws and do not, to the greatest possible extent, have hardened material, and a means for interlocking with the bone screws, e.g. a material lip, can be provided in the edge region of the holes.

In addition to the region of the load carrier bridging the fracture or instability zone, the regions around the first holes of the load carrier at the fracture or instability zone in particular are particularly prone to fracturing; as mentioned initially. Approximately 50-60% of all loads and forces are transferred through this region. In accordance with a preferred embodiment of the invention, this particularly heavily utilized region has an increased material strength. Said material strength is preferably increased by at least 40%, preferably by at least 60%, more preferably by at least 80% in the most heavily loaded region compared to the material strength in said region before the deformation.

At possible additional holes, which are located distally from the first holes, the load carrier does not need to have regions of increased material strength. However, since it can be assumed that, as mentioned initially, the load carrier must also endure an increased load at the following holes, the next hole and the next hole which may follow after that also have an increased material strength in the regions around the holes, which material strength is reduced with increasing distance from the fracture or instability zone of the bone in accordance with the load in these regions. By way of example, the material strength in the case of a load carrier is thus only approximately half the strength in the region around the second hole when compared to the material strength in the region around the first hole, and the material strength in the region around the third hole is at most half the strength of the material strength in the region around the second hole. Expediently, the material strength in the load carrier varies continuously at the transition from regions of increased material strength to regions of reduced material strength.

BRIEF DESCRIPTION OF THE DRAWINGS

The invention will be explained in more detail below on the basis of the attached drawings of exemplary embodiments. In the drawings.

FIG. 7 shows a cross-sectional section of the bone plate semi-finished product after the deformation; and FIG. 8 shows a cross-sectional section through a hole of a hardened 6-hole bone plate.

DESCRIPTION OF THE INVENTION

Figure 1:
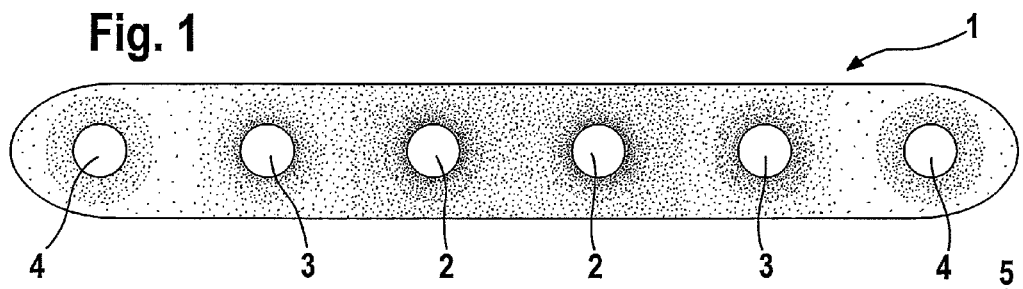
FIG. 1 shows a plan view of a 6-hole bone plate according to the invention.
Figure 2:
FIG. 2 shows a longitudinal section of a 6-hole bone plate semi-finished product.

FIG. 1 shows a 6-hole bone plate 1, as can be obtained from the 6-hole bone plate semi-finished product 5 as illustrated in FIG. 2. The bone plate 1 has in each case a pair of holes 2, 3 and 4. Of these, the plate hole 2 is arranged proximally, the plate hole 4 is arranged distally and the plate hole 3 is arranged between the plate holes 2 and 4 with respect to the fracture or instability zone of a bone. The bone plate 1 has a region of increased material strength around the hole 2, and, compared to the region around the hole 2, a region of reduced material strength around the hole 3 and a region of even more reduced material strength around the hole 4. The material strength of these regions corresponds to their load transmission which is approximately 50-60% in the region around the plate hole 2, approximately 20-30% in the region around the plate hole 3 and approximately 10% in the region around the plate hole 4. The strength of the material strength is illustrated schematically by the strength of the shading. The material strength is strongest in the regions with strong shading. The bone plate 1 has a planar top and bottom side. The different material strengths in the regions of the bone plate 1 correspond to the material volume of the bone plate semi-finished product 5 present in these regions before the pressing procedure to increase the material density, as illustrated in FIG. 2. The lateral section of the bone plate semi-finished product 5 in FIG. 2 shows that the bone plate semi-finished product 5 has different thicknesses and holes. The bone plate semi-finished product 5 can be formed to be planar on the top and bottom side by using a shaping press-form tool with planar faces so that part of the material flows into the holes of the bone plate semi-finished product 5 during the deformation.

Figure 3:
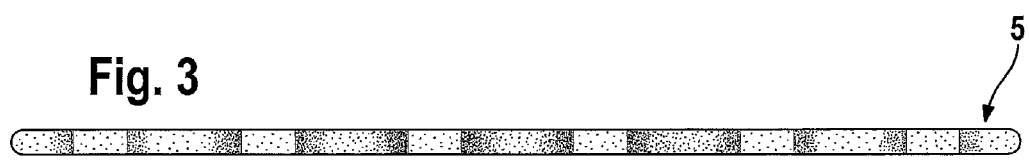
FIG. 3 shows a longitudinal section of a 6-hole bone plate semi-finished product after the deformation.
Figure 4:
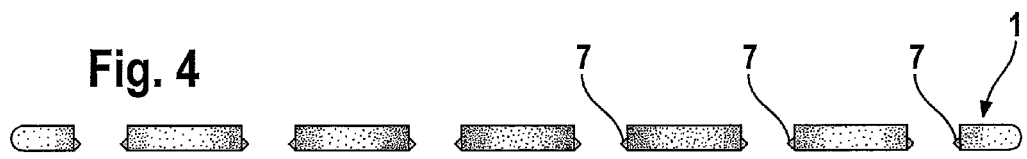
FIG. 4 shows a longitudinal section of a 6-hole bone plate according to the invention.

The bone plate semi-finished product 5 obtained after the deformation is illustrated in FIG. 3. The material which has flowed into the holes during the deformation is not significantly hardened so that during reworking this can be processed into a soft material lip 7 for deforming and interlocking with the screw head, as illustrated in FIG. 4.

Figure 5:
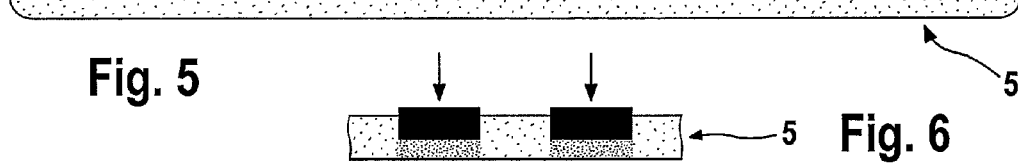
FIG. 5 shows a hardened press form for a 6-hole bone plate which acts on a bone plate semi-finished product.

FIG. 5 shows a soft bone plate semi-finished product 5 onto which a hardened press form with holes is pressed in the direction of the arrow. During the pressing procedure, the soft material of the bone plate semi-finished product 5 flows back into the holes of the forming tool.

Figure 6:
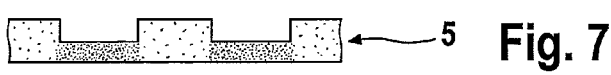
FIG. 6 shows a cross-sectional section from FIG. 5 during the deformation.
Figure 5:
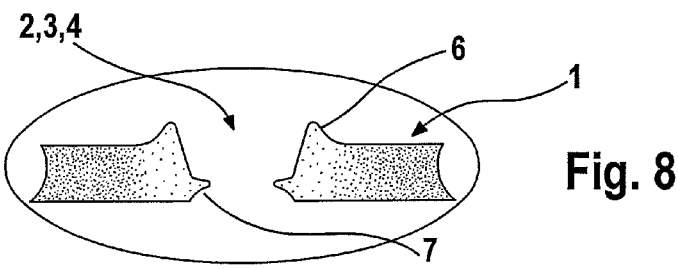

FIG. 6 shows a section of the material backflow into the holes when the press form is pressed onto the soft bone plate semi-finished product 5 while forming the material mushroom at the deformed bone plate semi-finished product 5 visible in FIG. 7.

FIG. 8 shows that region of the material mushroom from FIG. 7 which was reworked. The soft material of the material mushroom serves as the material of the wall of the hole of the bone plate 1, from which a horizontal material lip 7 and an annular wall 6 around the hole 2, 3, 4 were carved out. The annular wall 6 increases the stability in the region of the hole and screens the screw head (not illustrated) from the tissue lying on it (not illustrated), so that the latter is not irritated by sharp parts of the screw head.

The invention claimed is:

1. A load carrier for a bone fixation system, wherein the load carrier has a locally varying and shape independent material strength with substantially unchanging material elasticity, the load carrier comprises a hole for holding a bone screw, and the load carrier has a locally increased and shape independent material strength in a region around the hole, and wherein a wall of the hole in the load carrier is provided with an interlock for interlocking with the bone screw.

2. The load carrier of claim 1, wherein the locally varying material strength of a region of the load carrier corresponds to a respective load acting on the region.

3. The load carrier of claim 1 or 2, wherein the load carrier comprises two adjacent holes for holding bone screws, which are to be arranged on different sides of a fracture or instability zone of a bone, and the load carrier has a locally increased and shape independent material strength in regions around the adjacent holes or in the regions around the adjacent holes and a region bridging the fracture or instability zone between the adjacent holes.

4. The load carrier of claim 3, wherein the load carrier comprises a first at least one further hole arranged more distally from the fracture or instability zone of the bone compared to the two adjacent holes.

5. The load carrier of claim 4, wherein the load carrier has an increased and shape independent material strength in the region around the first at least one further hole as a result of material compression, the material strength in the region around the first at least one further hole being less than the material strength in the region around the two adjacent holes.

6. The load carrier of claim 5, wherein the load carrier comprises a second at least one further hole arranged more distally from the fracture or instability zone of the bone compared to the first at least one further hole, and has increased and shape independent material strength in the region around the second at least further hole as a result of material compression, the material strength in the region around the second at least one further hole being less than the material strength in the region around the first at least one further hole.

7. The load carrier of claim 3, wherein a wall of each hole in the load carrier is provided with an interlock for interlocking with a bone screw.

8. The load carrier of claim 3, wherein the load carrier is a bone plate, a bone nail or a fixator.

9. The load carrier of claim 3, wherein at least one of a top side and a bottom side of the load carrier is planar.

10. The load carrier of claim 3, wherein the load carrier comprises metal or metal alloy.

11. A method for producing a load carrier, comprising:
a) providing a load carrier semi-finished product having a greater material volume in regions of the load carrier intended to have a higher material strength than in regions intended to have a lower material strength; and
b) deforming the load carrier semi-finished product using a shaping press-form tool.

12. The method of claim 11, wherein in step b), the fibers of a fibrous material contained in the load carrier semi-finished product align at least in part in the direction of a main loading axis of the load carrier.

13. The method of claim 11 or 12, wherein the deformation is effected by cold forming.

14. The method of claim 11, wherein in step b), the height of the load carrier semi-finished product is reduced perpendicular to a deformation force in the regions intended to have a higher material strength.

15. The method of claim 11, wherein the load carrier semi-finished product is deformed between an upper tool and lower tool determining the shape of the load carrier.

16. The method of claim 15, wherein at least one of the upper tool and the lower tool have receptacles which prevent significant material hardening in the regions of the load carrier semi-finished product that lie opposite the receptacles during the deformation in step b) and in which holes for attaching the load carrier to a bone are provided.

17. The method of claim 16, further comprising:
c) holing regions which lie opposite the receptacles during the deformation in step b) and in which holes for attaching the load carrier to the bone are provided; and
d) providing an edge of each hole which does not comprise hardened material with an interlock for interlocking with a bone screw.

18. The method of claim 17, wherein the interlock comprises a material lip.

19. The method of claim 15, wherein at least one of the top and bottom side of the load carrier semi-finished product is shaped to be planar on one or two sides by a corresponding surface of at least one of the upper tool and the lower tool.

20. The method of claim 15, wherein at least one of the upper tool and the lower tool have inward or outward molding, in the corresponding regions of the load carrier intended to have higher material strength, which image mirror-symmetrically in the surface of the pressed load carrier.

21. The method of claim 11, wherein after the deformation step b), the load carrier has at least one region in which the material strength is increased by at least 40% compared to the material strength in the at least one region before the deformation.

22. The method of claim 21, wherein after the deformation step b), the load carrier has at least one further second region in which the material strength is less than the material strength of the at least one region and higher than the material strength in the at least one further second region before the deformation.

23. The method of claim 22, wherein after the deformation step b), the load carrier has at least one further third region in which the material strength is less than the material strength of the at least one further second region and higher than the material strength in the at least one further third region before the deformation.

* * * * *